＝

US008071322B2

(12) United States Patent
Zhang

(10) Patent No.: US 8,071,322 B2
(45) Date of Patent: Dec. 6, 2011

(54) METHOD FOR IDENTIFYING DIFFERENTIALLY EXPRESSED PROTEINS

(75) Inventor: Dongxiao Zhang, Moraga, CA (US)

(73) Assignee: Epitomics, Inc., Burlingame, CA (US)

( * ) Notice: Subject to any disclaimer, the term of this patent is extended or adjusted under 35 U.S.C. 154(b) by 1879 days.

(21) Appl. No.: 10/705,109

(22) Filed: Nov. 10, 2003

(65) Prior Publication Data

US 2005/0009118 A1    Jan. 13, 2005

Related U.S. Application Data

(60) Provisional application No. 60/426,029, filed on Nov. 12, 2002.

(51) Int. Cl.
  G01N 33/53    (2006.01)
  G01N 33/554    (2006.01)
  G01N 33/574    (2006.01)
(52) U.S. Cl. ............. 435/7.23; 435/7.95; 435/69.3; 435/325; 435/969; 436/503; 436/518; 436/519; 436/172; 436/813
(58) Field of Classification Search .......... 435/7.23, 435/7.95, 69.3, 32.5, 969; 436/503, 518, 436/519, 172, 81.3
See application file for complete search history.

(56) References Cited

U.S. PATENT DOCUMENTS

| | | | | |
|---|---|---|---|---|
| 4,880,750 | A * | 11/1989 | Francoeur | 436/501 |
| 4,892,934 | A * | 1/1990 | Yoshida et al. | 530/388.8 |
| 5,270,167 | A * | 12/1993 | Francoeur | 435/7.21 |
| 5,506,126 | A | 4/1996 | Seed et al. | |
| 5,675,063 | A * | 10/1997 | Knight | 800/14 |
| 5,703,057 | A * | 12/1997 | Johnston et al. | 514/44 |
| 5,851,764 | A * | 12/1998 | Fisher et al. | 435/6 |
| 5,939,286 | A * | 8/1999 | Johnson et al. | 435/69.51 |
| 6,541,011 | B2 * | 4/2003 | Punnonen et al. | 424/204.1 |
| 6,943,236 | B2 * | 9/2005 | Xu et al. | 530/350 |
| 6,989,276 | B2 * | 1/2006 | Thompson et al. | 436/518 |
| 2003/0044849 | A1 * | 3/2003 | Kessler | 435/7.1 |

OTHER PUBLICATIONS

Handa et al., 1997. A new procedeure for establishing functional monoclonal antibodies capable of inhibiting E- or P-selectin-dependent cell adhesion. Glycoconjugate Journal 14: 39-43.*
Krueger et al., 2003. A new small cell lung cancer (SCLC)-specific marker discovered through antigenic subtraction of neuroblastoma cells. Cancer Immunol. Immunother. 52:367-377.*
Pfreundschuh et al., 1978. Serological analysis of cell surface antigens of malignant brain tumors. Proceedings of the National Academy of Sciences USA 75 (10): 5122-5126.*
Goding, 1983. Monoclonal Antibodies: Principles and Practice, Academic Press, London. pp. 250-261.*
Bickel et al., Use and Applications of Subtractive Antibody Screening, Biotechnol Genet. Eng. Rev. 2000, 17: 417-30.
Scherer et al., Cloning of Cell-Specific Secreted and Surface Proteins by Subtractive Antibody Screening, Nat. Biotechnol., 1998, 16: 581-6.
Shusta et al., Vascular Proteomics and Subtractive Antibody Expression Cloning, The Mol. Soc. For Biochem. And Molecular Biol., 2002, 75-82.
Zannettino et al., A Powerful New Technique for Isolating Genes Encoding Cell Surface Antigens Using Retroviral Expression Cloning, J. Immunol., 1996, 156: 611-20.

* cited by examiner

*Primary Examiner* — Gail R Gabel
*Assistant Examiner* — James L Grun
(74) *Attorney, Agent, or Firm* — James S. Keddie; Bozicevic, Field & Francis

(57) ABSTRACT

The invention provides a method of identifying an antigen that is present in different amounts in two different samples. In general, the methods involve generating a first and second distinguishably labeled population of antibodies that reactive to the two samples, contacting the first and second labeled populations of antibodies with a plurality of antigens; and identifying any resultant antigens that are differentially bound by the first and second populations of antibodies. The antigens may be on the surface of cells e.g., animal cells, or on a solid support. Once identified, the nucleic acid encoding an antigen of interest may be identified and sequenced to reveal the identity of the antigen of interest. Kits for performing the methods are also provided. The methods find most use in medical and research applications, in particular, for identifying cell surface targets for immunotherapy and drug discovery.

7 Claims, 6 Drawing Sheets

SEQUENCE LISTING

<160> NUMBER OF SEQ ID NOS: 2

<210> SEQ ID NO 1
<211> LENGTH: 21
<212> TYPE: DNA
<213> ORGANISM: H. sapiens

<400> SEQUENCE: 1
ggctgccgac cccgggggtg g                    21

```
<210> SEQ ID NO 2
<211> LENGTH: 21
<212> TYPE: DNA
<213> ORGANISM: H. sapiens

<400> SEQUENCE: 2
cgaaccccag agtcccgctc a                                              21
```

METHOD FOR IDENTIFYING DIFFERENTIALLY EXPRESSED PROTEINS

CROSS-REFERENCING

This patent application claims priority to U.S. Provisional Patent Application No. 60/426,029, filed Nov. 12, 2002, which application is hereby incorporated by reference herein in its entirety for all purposes.

ACKNOWLEDGMENT OF GOVERNMENT SUPPORT

This invention was made with Government support under Grant No. DAMD17-03-C-0039 awarded by the U.S. Army. The Government has certain rights in this invention.

INTRODUCTION

1. Field of the Invention

The field of this invention is molecular biology. The invention relates to methods of identifying a protein that is differentially expressed between the samples, and isolating its encoding nucleic acid.

2. Background of the Invention

An enormous amount of effort is focused on understanding human diseases and conditions such as cancer, aging, abnormal development, cardiovascular disease and neurodegeneration. The genes that are abnormally expressed in these phenomena are of particular interest.

Several methods have been described for identifying mRNAs whose expression is associated with these phenomena. These methods include DNA microarrays (Schena et al Science 270:467-70, 1995), RNA display serial analysis of gene expression, subtraction hybridization, reciprocal subtraction differential RNA display, representational difference analysis, RNA fingerprinting by arbitrarily primed PCR, electronic subtraction, combinational matrix gene analysis, and signal sequence trapping (see U.S. Pat. No. 5,536,637).

However, these methods have several shortcomings.

One limitation is that changes in mRNA levels often do not correlate with changes in their encoded protein levels. As such, several "false positives" may be identified by the above methods.

Another limitation is that expression of a particular protein may be up-regulated without a concomitant increase in mRNA expression. Such an increase in gene expression would be undetectable using the above methods.

Another limitation is that a cell employs a wide variety of post-translational modifications to regulate the activity of a protein, and these modifications are undetectable using the above methods.

Furthermore, the preceding methods are not useful for identifying proteins that are localized in specific subcellular compartments such as cell membrane, nuclei, cytoplasm and extracellular space.

In one attempt to overcome these limitations, Scherer et al (Nat Biotechnol. 16:581-6, 1998) described a method that utilized immunodepleted rabbit polyserum to screen a cDNA bacteriophage cDNA library. This method involves raising polyclonal antibodies for a first cell type and immunodepleting the antibodies using a second cell type in order to isolate antibodies that are specific for the first cell type. While this method was successful for isolating a handful of cDNAs, methods using immunodepletion, in general, also have a number of serious limitations. Firstly, immunodepletion methods are tedious and most often involve more than one depletion procedure. Secondly, immunodepletion is never complete and the antibodies that are not removed by this procedure typically cause a large number of false positives. Thirdly, rare antibodies in the non-depleted antiserum may be depleted due to non-specific binding or carry-over by the depleting material.

As such, there is a need for improved methods for detecting and identifying gene products, especially proteins, that are abnormally expressed in human conditions and diseases. This invention meets these, and other needs.

LITERATURE

The following literature may be of interest: Scherer et al. (Nat Biotechnol. 16:581-6, 1998), Zannettino et al. (J Immunol 156:611-20, 1996), Bickel et al. (Biotechnol Genet Eng Rev 17:417-30, 2000), Shusta et al. (Molecular and Cellular Proteomics 1.1 75-82, 2001) and U.S. Pat. No. 5,506,126.

SUMMARY OF THE INVENTION

The invention provides a method of identifying an antigen that is present in different amounts in two different samples. In general, the methods involve generating a first and second distinguishably labeled population of antibodies that reactive to the two samples, contacting the first and second labeled populations of antibodies with a plurality of antigens; and identifying any resultant antigens that are differentially bound by the first and second populations of antibodies. The antigens may be on the surface of cells e.g., animal cells, or on a solid support. Once identified, the nucleic acid encoding an antigen of interest may be identified and sequenced to reveal the identity of the antigen of interest. Kits for performing the methods are also provided. The methods find most use in medical and research applications, in particular, for identifying cell surface targets for immunotherapy and drug discovery.

DEFINITIONS

Figure 1:
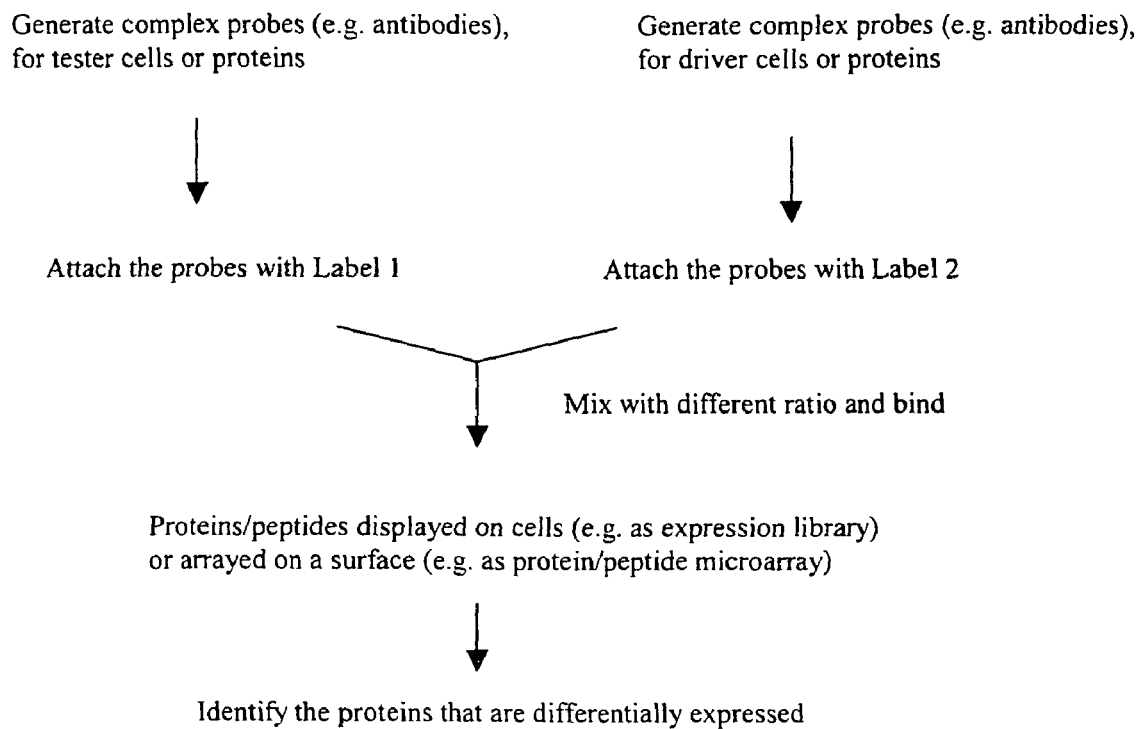
FIG. 1 is a schematic diagram of an embodiment of the present invention.

The terms "antibody" and "immunoglobulin" are used interchangeably herein. These terms are well understood by those in the field, and refer to a protein consisting of one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions.

The recognized immunoglobulin polypeptides include the kappa and lambda light chains and the alpha, gamma ($IgG_1$, $IgG_2$, $IgG_3$, $IgG_4$), delta, epsilon and mu heavy chains or equivalents in other species. Full-length immunoglobulin "light chains" (of about 25 kDa or about 214 amino acids) comprise a variable region of about 110 amino acids at the $NH_2$-terminus and a kappa or lambda constant region at the COOH-terminus. Full-length immunoglobulin "heavy chains" (of about 50 kDa or about 446 amino acids), similarly comprise a variable region (of about 116 amino acids) and one of the aforementioned heavy chain constant regions, e.g., gamma (of about 330 amino acids).

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. Also encompassed by the terms are Fab', Fv, $F(ab')_2$, and or other antibody fragments that retain specific binding to antigen.

Antibodies may exist in a variety of other forms including, for example, Fv, Fab, and $(Fab')_2$, as well as bi-functional (i.e. bi-specific) hybrid antibodies (e.g., Lanzavecchia et al., Eur. J. Immunol. 17, 105 (1987)) and in single chains (e.g., Huston et al., Proc. Natl. Acad. Sci. U.S.A., 85, 5879-5883 (1988) and Bird et al., Science, 242, 423-426 (1988), which are incorporated herein by reference). (See, generally, Hood et al., "Immunology", Benjamin, N.Y., 2nd ed. (1984), and Hunkapiller and Hood, Nature, 323, 15-16 (1986),).

It is understood that the humanized antibodies designed and produced by the present method may have additional conservative amino acid substitutions which have substantially no effect on antigen binding or other antibody functions. By conservative substitutions is intended combinations such as gly, ala; val, ile, leu; asp, glu; asn, gin; ser, thr; lys, arg; and phe, tyr.

As used herein, the terms "determining," "measuring," and "assessing," and "assaying" are used interchangeably and include both quantitative and qualitative determinations.

The terms "polypeptide" and "protein", used interchangeably herein, refer to a polymeric form of amino acids of any length, i.e. greater than 2 amino acids, greater than about 5 amino acids, greater than about 10 amino acids, greater than about 20 amino acids, greater than about 50 amino acids, greater than about 100 amino acids, greater than about 200 amino acids, greater than about 500 amino acids, greater than about 1000 amino acids, greater than about 2000 amino acids, usually not greater than about 10,000 amino acids, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like. Also included by these terms are polypeptides that are post-translationally modified in a cell, e.g., glycosylated, cleaved, secreted, prenylated, carboxylated, phosphorylated, etc, and polypeptides with secondary or tertiary structure, and polypeptides that are covalently or non-covalently bound to other moieties, e.g., other polypeptides, atoms, cofactors, etc.

As used herein the term "isolated," when used in the context of an isolated antibody, refers to an antibody of interest that is at least 60% free, at least 75% free, at least 90% free, at least 95% free, at least 98% free, and even at least 99% free from other components with which the antibody is associated with prior to purification.

A "coding sequence" or a sequence that "encodes" a selected polypeptide, is a nucleic acid molecule which is transcribed (in the case of DNA) and translated (in the case of mRNA) into a polypeptide, for example, in vivo when placed under the control of appropriate regulatory sequences (or "control elements"). The boundaries of the coding sequence are typically determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral or procaryotic DNA, and synthetic DNA sequences. A transcription termination sequence may be located 3' to the coding sequence. Other "control elements" may also be associated with a coding sequence. A DNA sequence encoding a polypeptide can be optimized for expression in a selected cell by using the codons preferred by the selected cell to represent the DNA copy of the desired polypeptide coding sequence.

"Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence. Also encompassed are polypeptide sequences that are immunologically identifiable with a polypeptide encoded by the sequence.

"Operably linked" refers to an arrangement of elements wherein the components so described are configured so as to perform their usual function. Thus, a given signal peptide that is operably linked to a polypeptide directs the secretion of the polypeptide from a cell. In the case of a promoter, a promoter that is operably linked to a coding sequence will direct the expression of a coding sequence. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

By "nucleic acid construct" it is meant a nucleic acid sequence that has been constructed to comprise one or more functional units not found together in nature. Examples include circular, linear, double-stranded, extrachromosomal DNA molecules (plasmids), cosmids (plasmids containing COS sequences from lambda phage), viral genomes comprising non-native nucleic acid sequences, and the like.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells, which can be accomplished by genomic integration of all or a portion of the vector, or transient or inheritable maintenance of the vector as an extrachromosomal element. Thus, the term includes cloning, and expression vehicles, as well as integrating vectors.

An "expression cassette" comprises any nucleic acid construct capable of directing the expression of a gene/coding sequence of interest, which is operably linked to a promoter of the expression cassette. Such cassettes can be constructed into a "vector," "vector construct," "expression vector," or "gene transfer vector," in order to transfer the expression cassette into target cells. Thus, the term includes cloning and expression vehicles, as well as viral vectors.

A first polynucleotide is "derived from" a second polynucleotide if it has the same or substantially the same nucleotide sequence as a region of the second polynucleotide, its cDNA, complements thereof, or if it displays sequence identity as described above. A first polynucleotide may be derived from a second polynucleotide if the first polynucleotide is used as a template for, e.g. amplification of the second polynucleotide.

A first polypeptide is "derived from" a second polypeptide if it is (i) encoded by a first polynucleotide derived from a second polynucleotide, or (ii) displays sequence identity to the second polypeptides as described above. The term "unit dosage form" as used herein refers to physically discrete units suitable as unitary dosages for subjects (e.g., animals, usually humans), each unit containing a predetermined quantity of an agent, e.g. an antibody in an amount sufficient to produce the desired effect in association with a pharmaceutically acceptable diluent, carrier or vehicle. The specifications for the novel unit dosage forms of the present invention will depend on a variety of factors including, but not necessarily limited to, the particular agent employed and the effect to be achieved, and the pharmacodynamics associated with each compound in the host.

A polynucleotide is "derived from" a particular cell if the polynucleotide was obtained from the cell. A polynucleotide may also be "derived from" a particular cell if the polynucleotide was obtained from the progeny of the cell, as long as the polynucleotide was present in the original cell. As such, a single cell may be isolated and cultured, e.g. in vitro, to form a cell culture. A nucleotide isolated from the cell culture is "derived from" the single cell, as long as the nucleic acid was present in the isolated single cell.

A cell is "derived from" a host if the cell was obtained from the host. The progeny of a progenitor cell are derived from the same host as a progenitor cell. A cell may be "derived from" the same species as the host if the cell was isolated from an animal of the same species as the host animal. For example, NIH 3T3 cells are derived from mouse, 240E cells are derived from rabbit, and DT-40 cells are derived from chicken. The progeny of a progenitor cell are derived from the same species as the progenitor cell.

An antigen is "native" to a cell if the antigen is usually expressed by the cell. For example, rabbit 240E cells express rabbit polypeptide antigens. An antigen is "not-native" to a cell if the antigen is not usually expressed by the cell. For example, rabbit 240E cells do not usually express human polypeptide antigens, i.e., a polypeptide encoded by the human genome, and, as such, a human polypeptide is not native to a rabbit 240E cell.

The terms "treatment" "treating" and the like are used herein to refer to any treatment of any disease or condition in a mammal, e.g. particularly a human or a mouse, and includes: a) preventing a disease, condition, or symptom of a disease or condition from occurring in a subject which may be predisposed to the disease but has not yet been diagnosed as having it; b) inhibiting a disease, condition, or symptom of a disease or condition, e.g., arresting its development and/or delaying its onset or manifestation in the patient; and/or c) relieving a disease, condition, or symptom of a disease or condition, e.g., causing regression of the condition or disease and/or its symptoms.

The terms "subject," "host," "patient," and "individual" are used interchangeably herein to refer to any mammalian subject for whom diagnosis or therapy is desired, particularly humans. Other subjects may include cattle, dogs, cats, guinea pigs, rabbits, rats, mice, horses, and so on.

Before the present subject invention is described further, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "an antibody" includes a plurality of such antibodies and reference to "a variable domain" includes reference to one or more variable domains and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF PREFERRED EMBODIMENTS

The invention provides a method of identifying an antigen that is present in different amounts in two different samples.

In general, the methods involve generating a first and second distinguishably labeled population of antibodies that reactive to the two samples, contacting the first and second labeled populations of antibodies with a plurality of antigens; and identifying any resultant antigens that are differentially bound by the first and second populations of antibodies. The antigens may be on the surface of cells e.g., animal cells, or on a solid support. Once identified, the nucleic acid encoding an antigen of interest may be identified and sequenced to reveal the identity of the antigen of interest. Kits for performing the methods are also provided. The methods find most use in medical and research applications, in particular, for identifying cell surface targets for immunotherapy and drug discovery.

In describing the invention, the compositions for use in the subject methods are described first, followed by a description of the methods themselves. Finally, kits for performing the subject methods are described, as well as several applications in which the subject methods find use.

Samples

The invention provides a method of identifying an antigen that is present in two samples, i.e., a first and a second sample, in differing amounts. Samples that are complex are usually used in the subject method, and accordingly, biological samples are usually used. By complex is meant that the samples contain a mixture of $10^5$, $10^6$, $10^7$, $10^8$ or $10^9$ or more different antigens, where an antigen is a target for an antibody. Accordingly, the samples used in the subject methods usually consist of a mixture at least $10^3$, $10^4$, $10^5$, etc., or more different constituents, e.g., proteins and the like. A suitable sample may be any sample that can act as an immunogen in an animal, e.g., a rabbit, mouse, chicken, etc., to produce a polyclonal antisera with an association constant of at least $10^5 M$ against the sample. In many embodiments, therefore, a sample is a cell, usually a pathogen or a mammalian cell or fraction thereof, and antigens of particular interest include those at the surface of the cell (i.e., antigens that are exposed to the outside of a cell and accessible to an antibody when the cell is intact). By "pathogen or mammalian cell" is meant a cell from a pathogen e.g. a bacteria or yeast, or a mammal, e.g., a human cell, or derivative thereof, including those cells grown in vitro, recombinant cells, cell fusions, and cells infected with a pathogen, and the like, etc. By "fraction of a cell" is meant a subset of the total constituents of a cell that has been separated from other constituents of the cell using any means, e.g., physical or biochemical mean. Fractions of a cell that are of interest include fractions containing membrane proteins, soluble proteins, plasma membrane proteins, nuclear extract, nuclear membrane proteins, and the like, and biochemical fractions such as those obtained by separating the constituents of a cell by chromatography, e.g., affinity chromatography. In most embodiments, samples contain proteins in their native conformation, i.e., the samples have not been treated in any way to denature or solubilize the proteins contained in the sample.

Accordingly, the subject methods may be used to investigate: the subcellular localization of proteins, secretion of proteins (e.g., hormones, cytokines, growth factors, extracelluar matrix proteins, etc.), cell surface proteins (including receptors, channels, transporters and adhesion molecules, etc.) intracellular proteins (including enzymes, metabolic machinery proteins, signaling proteins and structural proteins). As discussed above, physical separation of these different classes of proteins by biochemical methods is well developed in the art. In addition, methods have developed to isolate specific groups of cells from a given tissue. It is possible to purify specific class of proteins from a specific cell type before using these protein materials in the process of this invention.

As noted above, two different samples are usually used in the subject methods. In most embodiments, the two samples are pair of samples consisting of an "experimental" sample, i.e., a sample of interest, and a "control" sample to which the experimental sample may be compared. In many embodiments, therefore, the subject samples are pairs of cell types or fraction thereof, one cell type being a cell type of interest, e.g., abnormal cells, and the other a control, e.g., normal, cell type. If two fractions of cells are compared, the fractions are usually the same fraction from each of the two cells. In certain embodiments, however, two fractions of the same cell may be compared. Exemplary cell type pairs include, for example, cells isolated from a tissue biopsy (e.g., from a tissue having a disease such as colon, breast, prostate, lung, skin cancer, or infected with a pathogen etc.) and normal cells from the same tissue, usually from the same patient; cells grown in tissue culture that are immortal (e.g., cells with a proliferative mutation or an immortalizing transgene), infected with a pathogen, or treated (e.g., with environmental or chemical agents such as peptides, hormones, altered temperature, growth condition, physical stress, cellular transformation, etc), and a normal cell (e.g., a cell that is otherwise identical to the experimental cell except that it is not immortal, infected, or treated, etc.); a cell isolated from a mammal with a cancer, a disease, a geriatric mammal, or a mammal exposed to a condition, and a cell from a mammal of the same species, preferably from the same family, that is healthy or young; and differentiated cells and non-differentiated cells from the same mammal (e.g., one cell being the progenitor of the other in a mammal, for example). In one embodiment, cells of different type, e.g., neuronal and non-neuronal cells, or cells of different status (e.g. before and after a stimulus on the cells) may be used. In another embodiment of the invention, the experimental material is cells susceptible to infection by a pathogen such as a virus, e.g. human immunodeficiency virus (HIV), etc., and the control material is cells resistant to infection by the pathogen. In another embodiment of the invention, the sample pair is represented by undifferentiated cells, e.g., stem cells, and differentiated cells.

Accordingly, the methods usually involve administering two samples, an experimental sample and a control sample, each containing a plurality of different isolated antigens to different animals of the same species (e.g., two rabbits) such that antibodies that bind at least a subset of the plurality of different antigens of each sample are made by the animal (i.e. greater than 10%, greater than about 20%, greater than about 40%, greater than about 60%, greater than about 70%, greater than about 80% or even greater than about 90% or even greater than about 95%, up to 100% of the antigens). In most embodiments, the antigens are biopolymers such as different polypeptides, oligopeptides, proteins, protein fragments, nucleic acids, polysaccharides, carbohydrates, lipids or oils, other molecules such as small inorganic or organic molecules, or mixtures or modified variants thereof, particularly those found on the surface of a cell. In many embodiments in which cellular samples are used, the cells are usually derived from a different species to the animal to be immunized by the sample. For example, if human samples are of interest, then rabbits, chickens or mice, etc., may be immunized.

Procaryotic (e.g. bacterial) and eucaryotic (e.g. insect, vertebrate, mammalian, human) cells or tissues may be used as samples. Human cells and tissues include, but not limited to, epithelial cells, endothelial cells, fibroblasts, nervous tissue cells, immune cells, muscle cells, hepatocytes, immoralized cells, malignant cells, viral infected cells and cells in a particular physiological and pathological state, etc.

In most embodiments, an antigen is a polypeptide, and the polypeptide is from about 9-about 15 amino acids in length, about 16 to about 40 amino acids in length, about 41 to about 60 amino acids in length, about 61 to about 100 amino acids in length, about 101 to about 200 amino acids in length, about 201 to about 300 amino acids in length, about 301 to about 400 amino acids in length, about 401 to about 500 amino acids in length, usually less than about 1000 amino acids in length.

Antibodies

In general, the methods involve immunizing a pair of identical animals (i.e., genetically identical or inbred animal), for example a pair of suitable mammals such as mice, rabbits, guinea pig, or a suitable avians, such as a chickens, with a sample pair, as described above, such that the animals produce antibodies against the samples. If the samples are cells, they may be termed "cellular immunogens". A cellular immunogen comprises more than about $10^4$, more than about $10^5$, more than about $10^6$, more than about $10^7$, more than about $10^8$, and usually no more than about $10^9$ or $10^{10}$ cells.

In most embodiments, the cells of a cellular immunogen are usually derived from a species different to the animal being immunized (e.g., if the cells are human cells, the cells may be used to immunize rabbits), and, accordingly, the animals usually mount an immune response against the cells. In certain embodiments, the cells are immortalized cells, and cells may be administered as living cells.

Methods of immunizing animal, including the adjuvants used, booster schedules, sites of injection, suitable animals, etc. are well understood in the art, e.g., Harlow et al. (*Antibodies: A Laboratory Manual*, First Edition (1988) Cold spring Harbor, N.Y., and Harlow, supra), and administration of living cells to animals has been described for several mammals and birds, e.g., McKenzie et al (Oncogene 4:543-8, 1989), Scuderi et al (Med. Oncol. Tumor Pharmacother 2:233-42, 1985), Roth et al (Surgery 96:264-72, 1984) and Drebin et al (Nature 312:545-8, 1984).

In many embodiments more than about $10^4$, more than about $10^5$, more than about $10^6$, more than about $10^7$, more than about $10^8$, and usually no more than about $10^9$ or $10^{10}$ antigens (or cells) are administered to the animal provide for antibodies against the antigens.

After the animals have been immunized, the animals usually mount an immune response against the plurality of antigens, and the blood of such animals will normally contain polyclonal antisera that bind (e.g., by ELISA, western blot, etc.), depending on how the methods are performed, at least about 5%, at least about 10%, at least about 20%, at least about 30%, at least about 40%, at least about 50%, at least about 80%, usually not more than about 90% or 95% or 100% of the plurality of antigens. Binding affinities of the polyclonal antisera to the antigens may vary between antigen, but will generally be in the range of at least about $10^6 M^{-1}$ at least about $10^7 M^{-1}$, at least about $10^8 M^{-1}$, or at least about $10^9 M^{-1}$ to $10^{10} M^{-1}$) for the cells. Polyclonal antisera are usually harvested in the immunized animals using methods well known in the art and used in the subject methods.

Accordingly, two antisera are usually produced, one for each of the two samples.

Libraries

A variety of libraries may be used in the subject methods, including cell and bacteriophage cDNA expression libraries, such libraries are well known in the art (see Ausubel and Sambrook, supra) and need not be discussed here in any more detail. In most embodiments, the libraries are made from the experimental sample, e.g., the library may be a cDNA library made from RNA isolated from the cells of the experimental sample, or a sample similar thereto.

In certain embodiments, the subject libraries may be provided by introducing cDNA vectors, e.g., a plurality of retroviral vectors containing individual cDNAs, or the like, into suitable animal cells. For example, a retroviral cDNA library may be made from cells of an experimental sample and introduced into host cell of a different species to the experimental cells in order to provide for expression of the experimental sample proteins. In many embodiments, the cDNA libraries are introduced into host cells are from the same species as the animal that was immunized with the host cells. For example, if the experimental sample cells are human cells, the host cells into which the cDNAs are made from the experimental sample cells are introduced may be a non-human animal cell, e.g., a mouse, rabbit, hamster, goat, chicken or avian (chicken) cell, depending on the animal used for immunizations. For example, if a mouse, chicken or rabbit is immunized, the host cell for a library may be a mouse cell (e.g., NIH 3T3), a chicken cell (e.g., DT-40) or a rabbit cell (e.g., 240E), etc. Animal cells usually correctly post-transcriptionally modify, target and fold other animal proteins, and, as such are most usually used in the subject methods.

Accordingly, in many embodiments, the animal cell libraries produce antigens that are not native to the host cells used, i.e., are not usually expressed in the host cells, and are usually derived from a different species than the host cells. For example, if a host cells are rabbit host cells, the antigens may be human or mouse polypeptides, and if the host cells are mouse host cell, the antigens may be a human or rabbit polypeptides.

In most embodiments, therefore, a plurality of different antigens is expressed in a population of host cells through introduction of a plurality of different nucleic acids encoding the antigens. In most embodiments, the nucleic acids are comprised within expression cassettes.

A library of different nucleic acids is usually transferred into a population of host cells such that the population of host cells produces the plurality of antigens. In some embodiments, the proteins are produced within the cell and the cell secretes and/or surface targets certain antigens. In certain embodiments, a single host cell may receive more than one antigen-encoding nucleic acid and may produce more than one antigen, whereas other cells may receive one antigen-encoding nucleic acid and produce one antigen. The population of cells, in general, is usually a mixture of single antigen and multiple antigen expressing cells, although populations in which single cells express single antigens and populations in which single cells express multiple antigens are also envisioned.

In one embodiment, the antigen encoding nucleic acids are nucleic acids identified as having a particular property, e.g., they may be differentially expressed in a disease such as a cancer, for example colon or breast cancer, or expressed in a certain tissue, or expressed at a certain time during normal or abnormal development, or encode polypeptides with certain activities, e.g. secreted polypeptides, membrane bound polypeptides, cell surface polypeptides, or have a certain other activity. Such nucleic acids may be identified using conventional gene expression (e.g., microarray), subtractive hybridization (see, e.g, J Cancer Res Clin Oncol. 1997; 123: 447-51 and Gene 2001 262:207-14), or conventional library screening technologies. Antigen encoding nucleic acids may also be unselected, meaning that they are not selected because of their expression pattern or activity of the antigen.

In certain embodiments, a plurality of expression cassettes containing different antigen-encoding nucleic acids is provided by a cDNA library, where the cDNA is cloned into a vector suitable for the expression the cDNA. Such vectors typically provide a promoter suitable for use in host cells operably linked to the cDNA, and as such, a plurality of such vectors will provide a plurality of expression cassettes for expression of different antigens in host cells. Exemplary vectors suitable for library construction include pCI from Promega (Madison, Wis.), Retro-X system from Clontech (Palo Alto, Calif.) and pCDNA3.1 from Invitrogen (Carlsbad, Calif.) and cDNA libraries in suitable vectors (e.g., retroviral expression libraries or plasmid expression libraries) can be purchased from Clontech (Palo Alto, Calif.) and Stratagene (La Jolla, Calif.) or from EdgeBiosystems (Gaithersburg, Md.). In certain embodiments, the vectors may contain secretion signal or cell surface targeting sequences, as described in further detail below.

By plurality is meant more than 1, for example more than 2, more than about 5, more than about 10, more than about 20, more than about 50, more than about 100, more than about 200, more than about 500, more than about 1000, more than about 2000, more than about 5000, more than about 10,000, more than about 20,000, more than about 50,000, more than about 100,000, usually no more than about 200,000. A "population" contains a plurality of items.

In many embodiments, the methods involve modifying host cells to make modified host cells that produce at least one antigen, e.g., at least one polypeptide, protein, fragment of a polypeptide or protein, post-translationally modified polypeptide etc. In certain embodiments, antigens are secreted from the modified host cells and/or targeted to the surface of the modified host cells such that antigenic epitopes of the polypeptide are presented on the outside of the cells. For example, a transmembrane receptor kinase may be targeted to the surface of an individual cell, and may present antigenic epitopes on the ligand binding domain on the outside of the cell.

In most embodiments, the modified host cells produce antigens in the modified host cells, which, in certain embodiments, may be post-transcriptionally and/or post-translationally modified in the modified host cells such that the polypeptides are cleaved, rearranged, covalently modified, e.g., glycosylated, phosphorylated, prenylated, acetylation, amidation, carbamylated, deamidation, farnesylated, formylation, geranyl-geranylated, methylated, or myristoylated, etc., as they would in a test cell.

In most embodiments, a single antigen of the plurality of antigens is encoded by a nucleic acid encoding at least the primary structure of the antigen, and the antigen-encoding nucleic acid is introduced into a host cell to provide for production of the antigen. In certain embodiments the nucleic acid encoding the antigen is a cDNA, sometimes a full-length cDNA, which means that the cDNA encodes a full length polypeptide. The sequence of the nucleic acid may be determined, may be partially determined, or may be unknown, and the nucleic acid may be selected, e.g., based on its expression under certain conditions, or may be unselected. In most embodiments, the nucleic acid is derived from a different species from which the host cell is derived, e.g., humans, if the host cell is a non-human animal. As such, the modified host cell is usually a recombinant host cell, and the antigen is encoded by a nucleic acid. In certain embodiments, the antigen is a post-translationally modified antigen and may have associated secondary, tertiary or quaternary structures.

A single antigen of the plurality is usually expressed in the modified host cell using an expression cassette containing a nucleic acid sequence encoding the antigen. Expression cassettes, including suitable promoters (e.g., inducible promoters) terminators, enhancers, translation initiation signals, translational enhancers, are well known in the art, and are discussed in Ausubel, et al, (Short Protocols in Molecular Biology, 3rd ed., Wiley & Sons, 1995) and Sambrook, et al, (Molecular Cloning: A Laboratory Manual, Third Edition, (2001) Cold Spring Harbor, N.Y.). Suitable promoters include SV40 elements, as described in Dijkema et al., EMBO J. (1985) 4:761; transcription regulatory elements derived from the LTR of the Rous sarcoma virus, as described in Gorman et al., Proc. Nat'l Acad. Sci USA (1982) 79:6777; transcription regulatory elements derived from the LTR of human cytomegalovirus (CMV), as described in Boshart et al., Cell (1985) 41:521; hsp70 promoters, (Levy-Holtzman, R. and I. Schechter (Biochim. Biophys. Acta (1995) 1263: 96-98) Presnail, J. K. and M. A. Hoy, (Exp. Appl. Acarol. (1994) 18: 301-308)) and the like. The expression polynucleotide provides expression cassettes for expression of an antigen in a host cell. In most embodiments, each expression cassette is more than about 0.5 kb in length, more than about 1.0 kb in length, more than about 1.5 kb in length, more than about 2 kb in length, more than about 4 kb in length, more than about 5 kb in length, and is usually less than 10 kb in length.

The expression cassette may be linear, or encompassed in a circular vector, which may further comprise a selectable marker. Suitable vectors, e.g., viral and plasmid vectors, and selectable markers are well known in the art and discussed in Ausubel, et al, (Short Protocols in Molecular Biology, 3rd ed., Wiley & Sons, 1995) and Sambrook, et al, (Molecular Cloning: A Laboratory Manual, Third Edition, (2001) Cold Spring Harbor, N.Y.). A variety of different genes have been employed as selectable markers, and the particular gene employed in the subject vectors as a selectable marker is chosen primarily as a matter of convenience. Known selectable marker genes include: the thimydine kinase gene, the dihydrofolate reductase gene, the xanthine-guanine phosporibosyl transferase gene, CAD, the adenosine deaminase gene, the asparagine synthetase gene, the antibiotic resistance genes, e.g., tetr, ampr, Cmr or cat, kanr or neor (aminoglycoside phosphotransferase genes), the hygromycin B phosphotransferase gene, and the like. Vectors may provide for integration into the host cell genome, or may be autonomous from the host cell genome.

In certain embodiments, an expression cassette further provides for targeting of the antigen to the surface of the host cell by producing an antigen operably linked to a cell surface targeting polypeptide. In such embodiments, the antigen encoding nucleic acid may be operably linked to a cell surface targeting polypeptide-encoding nucleic acid in the expression cassette, and transcription and subsequent translation of the nucleic acids provides for production of a fusion protein containing the antigen and the cell surface targeting polypeptide. As such, the expression cassette can provide for targeting of an antigen to the surface of a host cell, which antigen is not usually presented on the surface of the host cell. Suitable cell surface targeting polypeptides and their encoding nucleic acid sequences may be those of, for example, transmembrane serine threonine or tyrosine kinase receptors. Suitable cell surface targeting signals and their encoding nucleic acid sequences include receptor transmembrane domains, such as the epidermal growth factor receptor (EGFR) transmembrane domain (Ullrich, A. et al. Nature 309: 418-425 (1984)). In many embodiments, the cell surface targeting sequence is derived from the same species as the host cell. Further examples of strategies for targeting of polypeptides in a cell or protein secretion may be found in U.S. Pat. No. 6,455,247.

Expression cassettes may be introduced into a host cell using a variety of methods, including viral infection, transfection, conjugation, protoplast fusion, electroporation, particle gun technology, calcium phosphate precipitation, direct microinjection, viral vector delivery, and the like. The choice of method is generally dependent on the type of cell being transformed and the circumstances under which the transformation is taking place (i.e., in vitro). A general discussion of these methods can be found in Ausubel, et al, Short Protocols in Molecular Biology, 3rd ed., Wiley & Sons, 1995.

Accordingly, libraries may be produced using a number of means.

Methods

The invention thus provides a method for producing two polyclonal antisera, one directed to an "experimental" sample, usually containing at least one antigen, e.g., a protein, of interest, and a "control", that usually does not contain any antigens of interest. Accordingly, the invention provides two polyclonal antisera, one containing antibodies that specifically bind to antigens of interest, and another that does not. Identifying the antigens of interest is done by screening a library of antigens, e.g., one made from the "experimental" sample, as discussed above, and identifying antigens that bind to antisera made using the experimental sample in a higher amount than antisera made using the control sample. In particular embodiments, therefore, the methods involve differentially labeling the two polyclonal antibody populations, contacting the populations of labeled antibodies with a library of antigens under conditions suitable for the binding of the antibodies to the antigen, and identifying any antigens that are differentially bound by one population of antibodies as compared to the other. Antigens of interest may be identified because they are differentially bound by the polyclonal antisera, and this may be observed by assessing the relative levels of detectable labels bound to the antigen.

The subject populations of polyclonal antibodies may be differentially labeled using methods well known to the antibody arts (see e.g., Harlow and Lane (Using Antibodies: A Laboratory Manual, CSHL Press, 1999)). In particular, fluoroescent labels find use in the subject invention include xanthene dyes, e.g. fluorescein and rhodamine dyes, such as fluorescein isothiocyanate (FITC), 6-carboxyfluorescein (commonly known by the abbreviations FAM and F), 6-carboxy-2',4',7',4,7-hexachlorofluorescein (HEX), 6-carboxy-4',5'-dichloro-2',7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G (R6G$^1$ or G$^5$), 6-carboxyrhodamine-6G (R6G$^6$ or G$^6$), and rhodamine 110; cyanine dyes, e.g. Cy3, Cy5 and Cy7 dyes; coumarins, e.g umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc; BODIPY dyes and quinoline dyes. Specific fluorophores of interest that are commonly used in subject applications include: Pyrene, Coumarin, Diethylaminocoumarin, FAM, Fluorescein Chlorotriazinyl, Fluorescein, R110, Eosin, JOE, R6G, Tetramethylrhodamine, TAMRA, Lissamine, ROX, Napthofluorescein, Texas Red, Napthofluorescein, Cy3, and Cy5, etc. Antibodies may also be bound to chromogenic products.

In one embodiment of the invention, fluorocein (the active form is FITC) is used to label one antisera, while phycoerythrin (PE) is used to label the other antisera. In another embodiment, green fluorescent protein (GFP) is used to label one antisera, while a different fluorescent protein is used to label the other. In another embodiment of the invention, horseraddish peroxidase (HRP) is used to label one antisera, while alkaline phosphatase (AP) is used to label the other.

As mentioned above, the labels used in the subject methods are distinguishable, meaning that the labels can be independently detected and measured, even when the labels are mixed. In other words, the amounts of label present (e.g., the amount of fluorescence) for each of the labels are separately determinable, even when the labels are co-located (e.g., in the same tube or in the cell, plaque etc.). Suitable distinguishable fluorescent label pairs useful in the subject methods include Cy-3 and Cy-5 (Amersham Inc., Piscataway, N.J.), Quasar 570 and Quasar 670 (Biosearch Technology, Novato Calif.), Alexafluor555 and Alexafluor647 (Molecular Probes, Eugene, Oreg.), BODIPY V-1002 and BODIPY V1005 (Molecular Probes, Eugene, Oreg.), POPO-3 and TOTO-3 (Molecular Probes, Eugene, Oreg.), and POPRO3 TOPRO3 (Molecular Probes, Eugene, Oreg.). Further suitable distinguishable detectable labels may be found in Kricka et al. (Ann Clin Biochem. 39:114-29, 2002).

Once labeled, the two populations of labeled antibodies are used to screen a library of antigens to identify an antigen that is produced at a higher level in an experimental sample, as compared to a control sample. Since libraries of antigens may be obtained in a variety of formats, so, too, may be the screening methods. The conditions for antibody binding are generally those used for "Western blotting", library screening of bacteriophage expression libraries, and staining of cells with antibodies, as are well known in the art (See Harlow, Sambrook and Ausubel, supra).

Antigens of interest are usually identified because they are differentially bound by the labeled antibodies, and binding is assessed by assessing the level of antibody label associated with the antigen. In many embodiments, an antigen of interest is an antigen that is differentially bound by the antibodies such that the antigen is bound by experimental sample antibodies to provide a signal that is 2× greater, at least 5× greater, at least 10× greater, at least 20× greater, at least 50× greater or at least 100× greater, or more, as compared to the control sample antibodies, after any normalization of the signals has been performed.

The two labeled antisera are usually mixed in a suitable ratios, including an equimolar ratio, before binding to the library. In one embodiment of the invention, excess amount of the antisera for the "control" is mixed with antisera for the "experimental" sample so that only dominant species that are present in the antisera for the experimental sample but absent in the antisera for the control sample can bind to the displayed proteins. This stringent condition favors the selection of antigens of interest. In another embodiment of the invention, equimolar amounts of the antisera are mixed and allowed to bind to the displayed proteins or peptides. Antigens that are overexpressed or underexpressed in either of the samples may be assessed.

For example, traditional plaque or colony-based methods using cDNA expression libraries cloned into suitable vectors, e.g., bacteriophage lambda vectors may be used, where a library of polypeptides may be induced in a cell using IPTG, the cell lysed and the lysate linked to a solid support, e.g., a nylon membrane or the like, and the nylon membrane contacted with the antibodies under conditions suitable for antibody binding. Differentially labeled areas of the solid supports, corresponding to individual phage clones or colonies, may be identified.

In other embodiments, however, the library may be represented by an array of proteins. In this embodiment, an array containing a plurality of polypeptides is contacted with the pair of antibody populations, and polypeptides on the array that are differentially bound by the antibodies using methods that are typically used in the DNA array arts. Methods for making and using microarrays of polypeptides are known in the art (see e.g., U.S. Pat. Nos. 6,372,483, 6,352,842, 6,346, 416 and 6,242,266).

In many embodiments of particular interest, a cellular library, i.e., animal cells expressing a cDNA library derived from the experimental sample, as described above, may be used. In most embodiments, cells from the animal used for immunizations are used to host and express the library. Accordingly, animal cells producing antigens of the experimental sample cells may be made, and screened. Such cellular libraries are usually contacted with the two antibody populations under conditions suitable for antibody binding, and cells that are differentially bound by the antibody populations may be separated from other cells by, for example, flow cytometry, e.g. FACS. Method for performing flow cytometry are generally well known in the art. In general, these methods involve passing a plurality of cells singly through a detector, e.g., a fluorescence detector, and cells with desirable fluorescence are separated from other cells.

In one embodiment, host cells containing an expression library are cultured under condition suitable for expression of the experimental sample cDNA. The cells are then fixed and permeablized so that the proteins expressed within the cells are bindable by the antisera. The expression host cells are bound by the antisera. The host cells can be isolated by fluorescence-activated cell sorting or by affinity chromatography method, such as by using protein A-coated beads. The differentially stained cells are identified and isolated.

In another embodiment, host cells containing an expression library are fixed on a solid surface such as a tissue culture dish, with or without permeablization, before allowed to be bound by the complex probes. This process is well known in the art and is called immunostaining or immunocytochemistry. The differentially stained cells are identified and isolated.

The cDNA molecules that encode the displayed proteins can be isolated from the identified cells, cloned and sequenced. Accordingly, an antigen of interest may be identified using the subject methods.

As is well known in the art, once cells producing an antigen of interest are identified, the nucleic acid encoding the antigen of interest may be recovered from the cell using well known methods, e.g., plasmid rescue in bacteria, PCR, plasmid excision, etc., and sequenced and otherwise studied. The sequence of the nucleic acid encoding the antigen of interest becomes known, so too does the amino acid sequence of the antigen of interest.

Once the identity of the antigen of interest is known, monoclonal antibodies that specifically bind to the antigen of interest may be made by traditional methods (see Harlow, supra). In one embodiment, if a host cell from an animal is identified that produces the antigen of interest, that host cell may be cultured and used to inoculate a suitable animal, the suitable animal being of the same species as the host cell. Accordingly, polyclonal and monoclonal antibodies may be made for the antigen of interest.

With specific reference to FIG. 1, two antigen binding agent populations, i.e., complex probes, are produced, one for "tester" cells or proteins, and the other for "driver" cells or proteins. The two agent populations are labeled with labels 1 or 2, the labeled populations are mixed and contacted with a library of antigens, e.g., proteins presented on the surface of cells expressing a cDNA library, or an array of antigens on a solid support, and proteins that are differentially produced identified because they are differentially bound by the binding agent populations.

Figure 2:
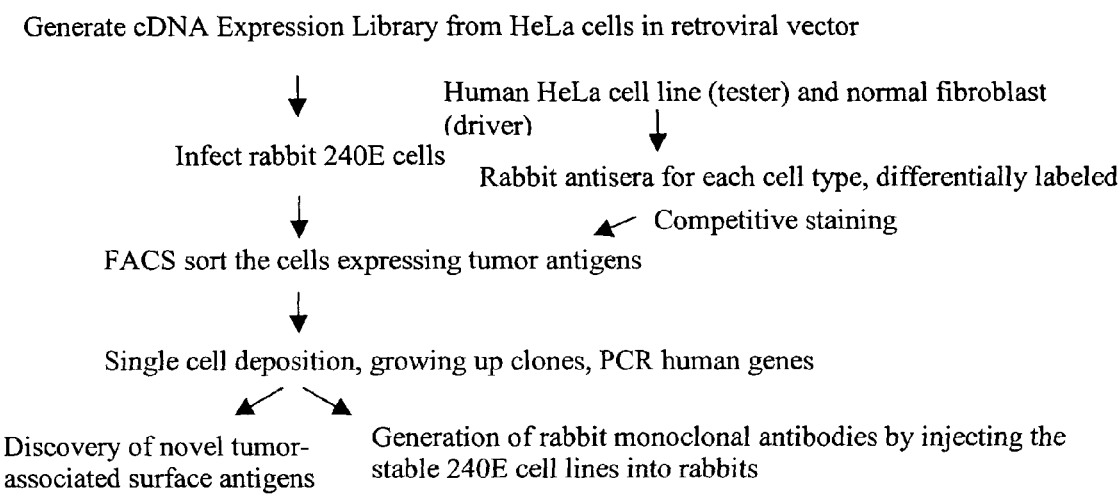
FIG. 2 is a schematic diagram of another embodiment of the present invention.

With specific reference to FIG. 2, a cDNA expression library is made from a suitable human cancer cell line (e.g., HeLa cells) and used to infect suitable non-human animal cells, e.g., rabbit 240E cells. A human cancer cell line (e.g., HeLa cells) and suitable non-cancerous control (e.g., normal fibrobast cells), are used to immunize suitable non-human animals, e.g., rabbits, to produce polyclonal antisera for the two cell types. The two antisera are differentially labeled and used to "competitively stain" the infected non-human animal cells. The stained cells are sorted by FACS according to their profile, deposited into culture media and cultured. The cells may be directly used immunize rabbits to make rabbit monoclonal antibodies. The cDNA contained in the sorted cells may be sequenced to identify tumor associated surface antigens.

It is recognized that the present invention provides for a method wherein the experimental and control samples are reversed to identify antigens which are either increasing or decreasing between two samples. In certain embodiments, the antibodies may be "phage-display" antibodies that are well known in the art, or other specific binding moieties, such as aptamers, etc.

Kits

Also provided by the subject invention are kits for practicing the subject methods, as described above. The subject kits at least include one or more of: an experimental and control sample, that, in particular embodiments are cellular samples, a cDNA library made from the experimental sample that may be present in animal cells, two antibody populations reactive against experimental and control samples, labeling reagents for labeling the antibodies, etc. Other optional components of the kit include: components for performing antibody binding assays, e.g., buffers, etc. The various components of the kit may be present in separate containers or certain compatible components may be precombined into a single container, as desired.

In addition to above-mentioned components, the subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Also provided by the subject invention is are kits including at least a computer readable medium including programming as discussed above and instructions. The instructions may include installation or setup directions. The instructions may include directions for use of the invention with options or combinations of options as described above. In certain embodiments, the instructions include both types of information.

Providing the software and instructions as a kit may serve a number of purposes. The combination may be packaged and purchased as a means for identifying antigens that are present at different amounts between two samples, including present and absent.

Utility

The invention provides a method for identifying antigens, e.g., obtaining an amino acid sequence of an antigen, that is present in greater amounts in one sample as compared to another. Accordingly, these methods have several applications, a representative many of which will be described below.

In one embodiment, the identified antigen may be an a protein that is only present in abnormal, e.g., cancerous or pathogen-infected cells, as compared to normal, e.g., non-cancerous or non-pathogen-infected cells. Accordingly, such a protein may be used as a target for drug, e.g., antibody or small molecule, therapy. Drug screening assays, which are generally well known in the art, may be used to identify such drugs. In particular embodiments, since the identified antigen may be an antigen on the surface of a cell, the drugs, in particular monoclonal antibodies that specifically bind to the antigen, may be made and screened for cytotoxic or other inhibitory activity against cells producing the identified antigen on the surface.

In another embodiment, the subject methods may be used in research, to understand the molecular events that are associated with an alteration of a cell (e.g., upon contacting the cell with a chemical or environmental stimulant, pathogen, or a change of a cell during its development, etc.).

In other embodiments, the subject methods may simply be used to investigate the differences between cell types, e.g., cells from two different tissues, or the like.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

DISC Technology

Dual Immunostaining-mediated Subtractive Cloning (DISC) technology may be used to identify disease-specific cell surface antigens, e.g. tumor-associated antigens (TAAs). Rabbit 240E cells are capable of expressing the entire range of human proteins, including normal and tumour-specific proteins. After infecting 240E cells with a HeLa cell cDNA library, some of the cells will express HeLa TAAs. A cell line expressing a particular TAA should preferentially bind a subset of the "anti-HeLa" polyclonal antibodies. In contrast, this same cell line should not bind the anti-NHDF (normal human dermal fibroblast) antibodies. By differentially labeling the two polyclonal antibodies and binding them competitively to the transformed 240E cell lines (i.e., showing competitive staining), we expect to highlight cells expressing TAAs and to sort them using FACS. After FACS analysis, the isolated TAA cell lines will be cultured and used in two ways. First, tumor antigen DNA will be amplified and sequenced. Second, stable TAA cell lines will be injected into rabbits to generate tumor antigen-specific antibodies. In fact, we have used 240E cells transfected with human genes to generate rabbit monoclonal Abs against numerous cell surface receptors.

Example 2

Generation of High Titer Rabbit Antiserum Against HeLa Cells and Normal Fibroblast Cells HeLa-S3 cells and normal human dermal fibroblast cells (NHDF) were grown to 80% confluency. Cells were detached using a non-enzymatic method (5 mM EDTA in culture medium) to minimize damage of membrane proteins. Cells were washed in PBS before s.c. injection into rabbits at $10^7$ cells/rabbit. Three rabbits were immunized as triplicate for each cell type. Due to the death of one NHDF rabbit, we used antisera from two rabbits that produced the highest titers in each group. Six sequential immunizations were carried out on a weekly basis. Titers were monitored using the cell-ELISA assay. Briefly, HeLa-S3 cells and fibroblasts were fixed in 96 well plates. Antisera from the immunized rabbits were serially diluted and applied to the fixed cells. Binding reactions were quantitated by peroxidase-conjugated anti-rabbit antibodies and chromogenic substrate diaminobenzidine (DAB) and confirmed by alkaline phosphatase-conjugated anti-rabbit antibodies followed by PNPP substrate. The titer of the polysera reached 1:50,000 for NHDF and 1:100,000 for HeLa.

Example 3

Purification of Polyclonal Antibodies From Antisera of Whole Cell Immunized Rabbits IgG from rabbits immunized with HeLa-S3 or NHDF cells were purified from the antisera with ImmunoPure Immobilized Protein G (Pierce # 20398). The elution of bound proteins was monitored by absorbance at 280 nm. The eluted immunoglobulin fractions were desalted with Pierce Desalting columns. Sample emergence was similarly monitored by measuring the absorbance of each fraction at 280 nm. 15 mgs of IgG were purified and pooled from 3 different bleeds of antisera from duplicate rabbits. 17 mgs of IgG were similarly obtained from the two NHDF immunized rabbits.

Example 4

Differential Labeling of the Purified IgG With Fluorescent Dyes

Anti-HeLa-S3 IgG was labeled with PE (phycoerythrin, MW 240,000). PE is a member of the phycobiliprotein family isolated from marine algae. The excitation and emission wavelengths of PE-labeled proteins are approximately 488 and 578 nm. PE was coupled to purified anti-HeLa antibodies as follows: Two heterobifunctional reagents succinimidyl 3-(2-pyridyldithio)propionate (SPDP) and succinimidyl trans-4-(maleimidylmethyl)cyclohexane-1-carboxylate (SMCC) were used. First, the lysine residues of PE are converted to a pyridyldisulfide derivative with SPDP, then reduced to thiol-PE with the reducing agent tris-(2-carboxyethyl) phosphine (TCEP). Second, lysines of the antibody are converted to thiol-reactive maleimides with a heterobifunctional crosslinking reagent, SMCC. Thiolated PE (PE-SH) and Ab-maleimide were mixed and crosslinked to each other through the formation of a stable thioether bond. The reaction was terminated by the addition of 20-fold molar excess of N-ethylmaleimide (NEM) to "cap" the remaining free thiols.

Anti-NHDF IgG was labeled with FITC (fluorescein isothiocynate, MW 389). FITC reacts with the primary amines of proteins to form the dye-protein conjugates. The excitation and emission wavelength of FITC-labeled proteins are approximately 494 nm and 520 mm, respectively. We found that the ratio of 50:1 (FITC:IgG) is optimal for FITC labeling.

Example 5

Production of Retroviruses Expressing HeLa cDNA Library, and Development of a Highly Efficient Protocol to Infect Rabbit 240E Cells A HeLa cell retroviral cDNA library was transformed into XL10-Gold *E. coli* cells and was then titered using serial dilution. To make library DNA, we then plated the XL10-Gold cells at a density of $1 \times 10^4$ in sixty 100 mm plates. Cells were grown at 37° C. overnight. 5 ml of LB medium was added per plate used to gently suspend the bacterial library using a cell scraper. The suspension was collected, pooled and incubate at 37° C. for no longer than 1 hr with constant shaking. HeLa expression library DNA was extracted with a QIAfilter plasmid kit. A total of 1.8 mg of plasmid library DNA was obtained. To generate retroviral particles, 293T cells were triple-transfected with an pFB XR plasmid cDNA library, made with a replication-defective vector, and with two additional packaging vectors pVPack-GP (gag-pol-expressing vector encoding internal structure proteins and reverse transcriptase) and pVPack-VSV-G (env-expressing vector encoding the viral envelope protein). Viral supernatant was collected 48-72 hrs post-transfection.

To determine viral infection rates in rabbit 240E cells, we infected 240E cells with pFB-Neo-LacZ, a plasmid that is similar to the library plasmid. Using standard retroviral infection methods, we found the titer of pFB-Neo-LacZ infection of 240E rabbit cells was 1-2%, however, we found that centrifugation of mammalian cells at 2400 rpm, 18° C. for 3 hrs in the presence of viral particles dramatically increased viral infection of all three cell lines up to 100 fold (to 70% transduced cells). Using beta-Gal as a reporter gene, we showed that, by in situ staining, 70% of 240E cells can be infected.

Example 6

Identification of "HeLa-Specific" cDNA-Expressing 240E Cells by FACS, Using Differentially Labeled Polyclonal Antibody Probes As mentioned above, the infected 240E cells that express HeLa cell surface antigens will be preferentially bound by the anti-HeLa polyclonal antibodies. Since the anti-NHDF antibodies should not recognize TAAs, we expect that the infected 240E cells expressing tumor-specific antigens will preferentially bind the anti-HeLa antibodies in a competition with both anti-HeLa and anti-NHDF polyclonal antibodies. Normal human surface antigens should be recognized by both the anti-HeLa and the anti-NHDF polyclonal preparations. 240E cells that do not express human proteins bind neither of the two polyclonal antibodies (see below).

240E cells, untreated or infected with the HeLa cell retroviral cDNA library ($7 \times 10^5$ cells/sample), were incubated in 100 µl of blocking buffer (1×PBS plus 2% FBS) at room temperature for 1 hr. Cells were stained with 4 µg of PE-conjugated anti-HeLa IgG, 4 µg of FITC-conjugated anti-NHDF IgG individually and in combination, and incubated on ice for 20-30 mins. In a parallel experiment, we performed an immuno-depletion step to remove potential non-specific antibodies that bind to rabbit 240E cells (referred as 240E-subtracted antibody). For this step, antibodies were incubated with $7 \times 10^5$ 240E cells in 100 µl of blocking buffer on ice for 30 mins. The 240E cells were then removed by centrifugation, and the remaining IgG in the supernatants was used to stain untreated or cells infected with the HeLa cell retroviral cDNA library. After the binding reaction, antibody-stained control and library-infected 240E cells were centrifuged at 1500 rpm for 5 min. After 2 washes with blocking buffer, cells were resuspended in 400 µl blocking buffer and kept at 4° C. in the dark before FACS analysis.

Example 6

Staining of 240E Cells and FACS Analysis

Figure 3:
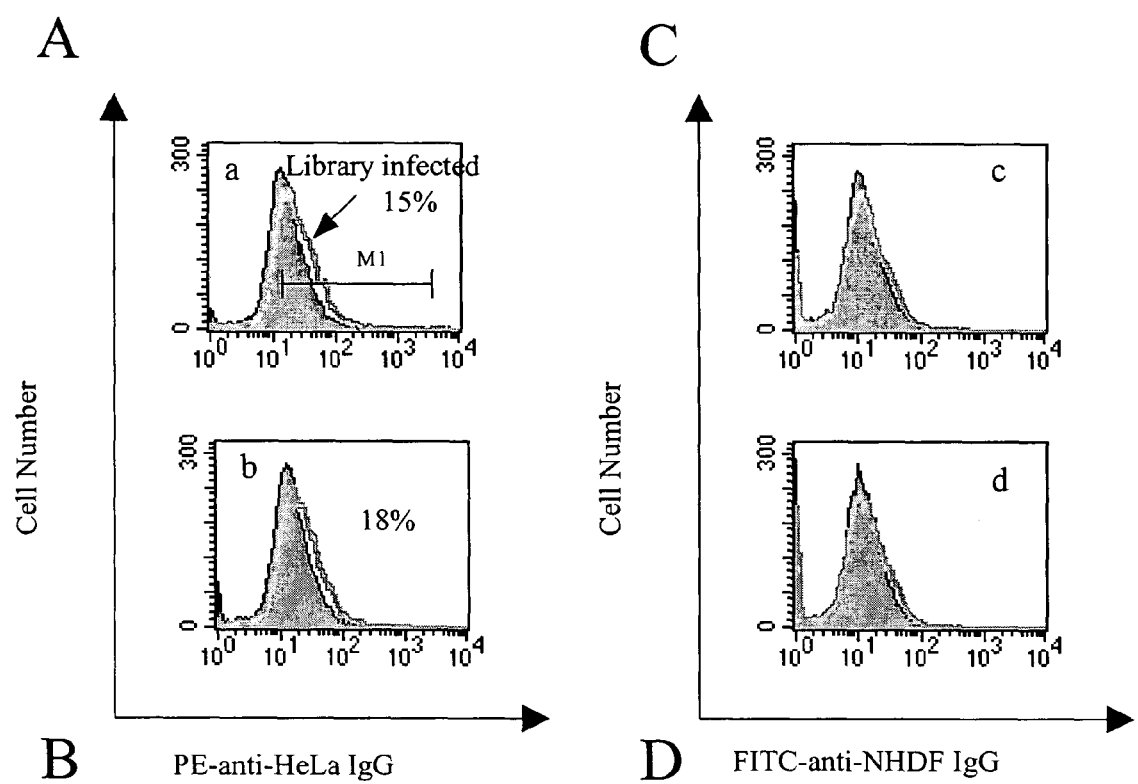
FIG. 3 shows four panels of graphs, A-D, showing FACS analysis of HeLa cDNA library-infected 240E cells. Cells were stained using either anti-HeLa (PE) or anti-NHDF (FITC) antibodies.

First, anti-HeLa (PE) and anti-NHDF (FITC) antibody probes were used individually to stain library infected and non-infected 240E cells. FIG. 3 shows 240E cells of non-infected control (black line with fill) and HeLa library-infected cells (line, no fill) are immunostained with PE-labeled polyclonal anti-HeLa antibody probe (a and b), or with FITC-labeled polyclonal anti-NHDF antibody probe (c and d). The antibody probes are either without pre-absorption (immuno-depletion) with 240E cells (a and c) or with immuno-depletion to decrease 240E background binding (b and d). Cells are subjected to flow cytometry on FACS Caliber machine. As shown in FIG. 3*a*, an apparent shift in cell population was observed when library-infected 240E cells are compared to non-infected cells, both stained with anti-Hela (PE) probes. With an arbitrary gating M1 and scoring 10,000 events for each cell population, 39.33% of control cells fall into the gate, whereas 65.77% of library-infected cells fall into the same gate. The difference (15%) reflects the difference based on this gating. Similar results were obtained with a slight improvement (18% difference) when 240E-subtracted antibody was used in the assay (FIG. 3*b*). This is expected, as IgG molecules that cross-react with 240E cells were removed before the binding reaction. In contrast, when anti-NHDF (FITC) probes were used (FIG. 3*c*), there is a very slight difference (less than 2%) between when library-infected 240E cells and non-infected cells. This reflects the fact that anti-NHDF antibodies recognize only a negligible fraction of HeLa surface proteins displayed on 240E cells in this cytometry setting. It is likely that when a higher number of library-infected cells is analyzed, the anti-NHDF antibodies will detect more HeLa proteins that share common epitopes (but the fraction will be the same). Similar results were obtained using the 240E-subtracted antibody probe (FIG. 3*d*).

Figure 4:
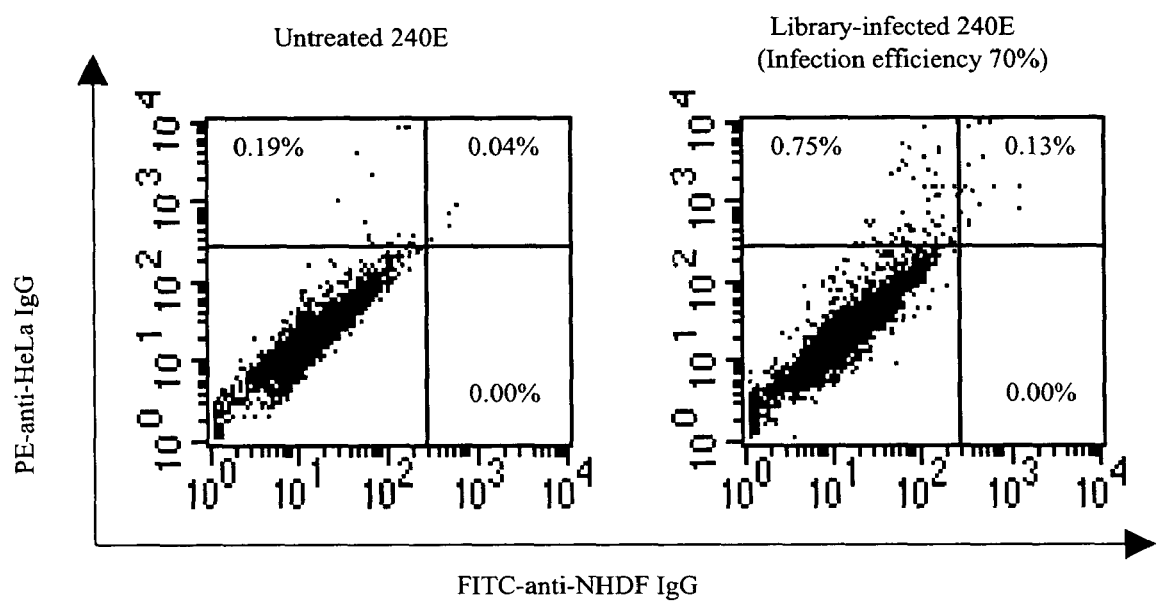
FIG. 4 shows two panels of graphs showing FACS analysis of HeLa cDNA library-infected 240E cells, competitively bound by anti-HeLa (PE) and anti-NHDF (FITC) antibody probes.

Second, anti-HeLa (PE) and anti-NHDF (FITC) antibody probes were simultaneously used to stain library infected or non-infected 240E cells (FIG. 4). FIG. 4 shows 240E cells of non-infected control (left panel) and HeLa library-infected cells (right panel) are immunostained with PE-labeled polyclonal anti-HeLa antibody probe and FITC-labeled polyclonal anti-NHDF antibody probe simultaneously. The antibody probes are without pre-absorption (immuno-depletion) with 240E cells. The antibody probes with immuno-depletion showed the same results (not shown). An equal amount (4 µg) of each type of antibody probe was added to the cells. 1) FACS analysis showed that the majority of cells are in the lower left quadrant, indicating that the majority of the library infected cells and control cells do not express surface antigens that are bound by the antibody probes. 2) Noticeably, cell numbers in the PE+/FITC− population (upper left quadrant) increased 4 fold from 0.19% for control 240E cells, to 0.75% for library-infected 240E cells. This indicates that this method distinguishes the cells that express HeLa specific cell surface genes, being bound only by anti-HeLa but not anti-NHDF antibodies. 3) There is also a 3 fold increase in the population of PE+/FITC+, from 0.04% for control cells to 0.13% for library-infected cells. This indicates the existence of common antigens that are recognized by antibodies for both HeLa and NHDF cell lines. 4) In agreement with the single probe binding assay, few cells were detected in the PE−/FITC+ quadrant. Anti-NHDF (FITC) antibody probes were shown in the same experiment to be able to stain NHDF cells (not shown).

Our experiments demonstrated that identification of rabbit cells expressing tumor specific surface markers is possible by using competitive immuno-staining with differentially labeled antibody probes. Our experiments showed that the rabbit 240E cell line is a valuable system for this technology. First, the cell line can be effectively infected using a retroviral expression library. Second, the cell line has very low background when an anti-human cell polyclonal antibody is used for staining. In fact, immunodepletion is not needed to remove antibodies that bind to rabbit cells. Third, the stable cell lines that are derived after FACS sorting can be used to immunize rabbits directly in order to generate rabMAbs against the stably expressed human cDNA. By defining an appropriate threshold (gate), a manageable number of PE+/FITC− cells can be sorted and studied.

Example 7

Confirmation of the Expression of Hela Proteins on 240E Clones and PCR Characterization of the Integrated Genes PCR and Cloning of the Hela Gene Integrated in 240E Cells Six clones were grown out of the single cells deposited in three 96-well plates. (Note: We have since optimized the condition for single cell growth, and expect a higher efficiency in the future.) Three clones (named Clone 2, 3 and 5) were further expanded in 24-well and then in 6-well plates, while the other 3 clones are in 96-well stage. DNA of these clones was extracted using QIAGEN genomic DNA purification kit. cDNA inserts were amplified using TaqPlus Precision PCR system (Stratagene), and 5'-Retro primer (5'-GGCTGCCGACCCCGGGGGTGG-3' (SEQ ID NO:1) and 3'-pFB (5'-CGAACCCCAGAGTCCCGCTCA-3' (SEQ ID NO:2)) as primers. Briefly, 2.5 ul 10× TaqPlus Precision buffer, 0.25 ul dNTP mix (25 mM of each nucleotide), 0.5 ul 5'-Retro primer (100 ng/ml), 0.5 ul 3'-pFB primer (100 ng/ml), and 0.5 ul TaqPlus Precision polymerase mixture were mixed and subjected to PCR reaction using MJ Research PTC-200 Thermal Cycler. The PCR program is as following:

1 cycle, 95 C for 1 min; 40 cycles, 95 C for 1 min, 64 C for 1 min, 72 C for 5 min; 1 cycle, 72 C for 10 min.

Figure 5:
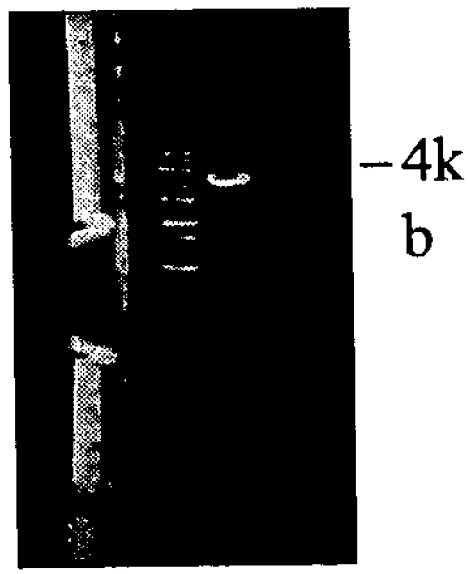
FIG. 5 shows a DNA gel showing PCR amplification of Hela genes from 3 of the 240E stable cell lines. 1 kb marker and clone numbers are indicated on the top. Clone 2 showed a specific PCR product.

As shown in FIG. 5, Clone 2 showed a single specific band, while some non-specific bands were observed for Clone 3. No PCR amplification was seen for Clone 5. TA cloning and sequencing of the PCR amplified product are in progress. Similar PCR amplification will be conducted for the rest of the clones.

FACS Analysis of the 240E Stable Clones

Figure 6:
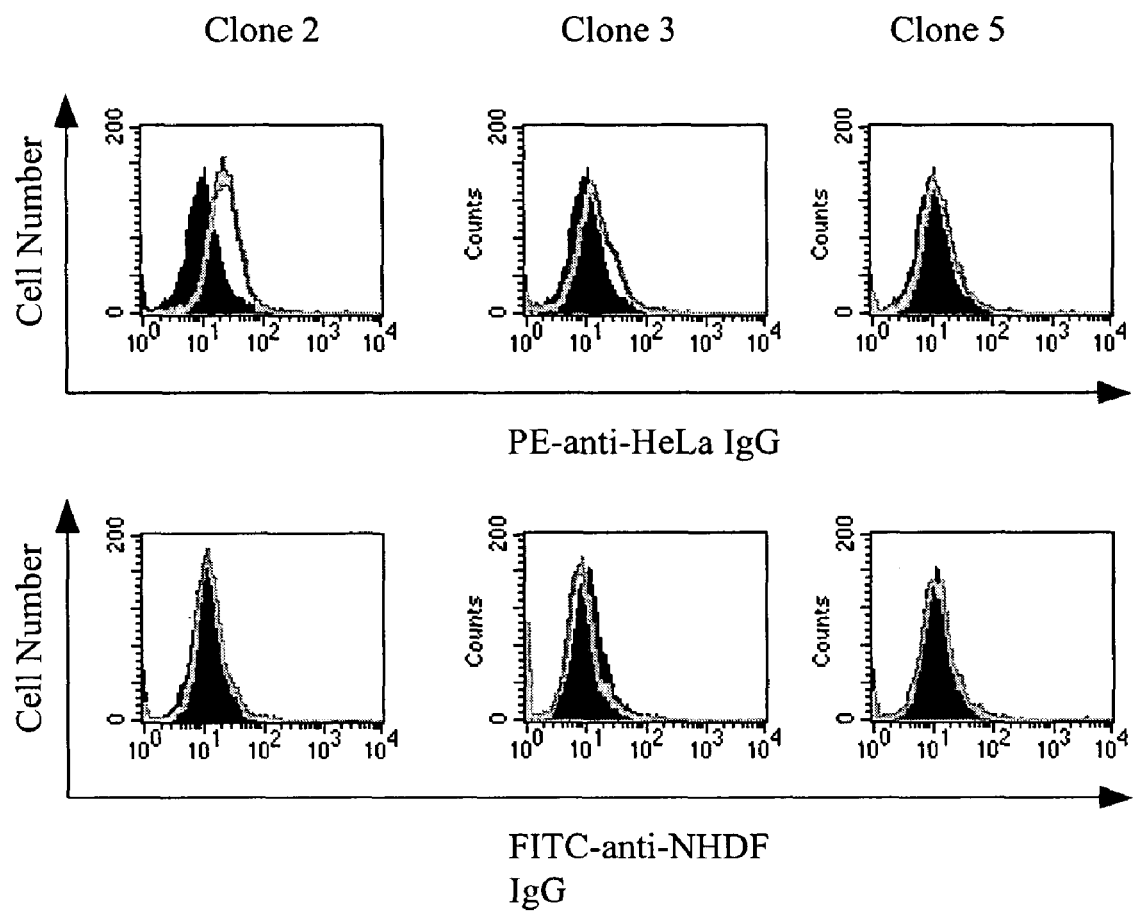
FIG. 6 shows six panels of graphs showing FACS analysis of the 240E stable clones

To confirm the expression of Hela-specific membrane proteins on the 240E stable cell lines, FACS analysis was used to analyze each of the three clones that have been analyzed by PCR (results shown in FIG. 6). In addition, Clone 6 which was yet examined by PCR was also included in the FACS experiment. Anti-Hela polyclonal antibody and anti-NHDF polyclonal antibody (Part 2) were used. The result of the FACS analysis is shown in FIG. 6. In agreement with the PCR result, Clone 2 showed specific binding by anti-Hela IgG, but not anti-NHDF IgG. Clone 3 and 5 did not show apparent IgG binding. We also found that Clone 6 express high levels of Hela-specific membrane protein (data not shown). The integrated DNA sequence will be determined for all of the positive clones. It can be concluded that DISC is an efficient technique to clone genes of cell-specific membrane proteins.

In certain embodiments of the invention, the complex probe is a plurality of artificial binding proteins, e.g., protein domains such as fibronectin domains can be randomized and used as a library of binding proteins to a target.

In another embodiment of the invention, the complex probe is nucleic acid molecules such as aptomers. It is known that nucleic acid molecules can adopt different conformations and binding to proteins with certain affinity.

It is evident from the above results and discussion that the subject invention provides an important new means for identifying an antigen that is differentially expressed between two cell types, or fractions thereof. As such, the subject methods and systems find use in a variety of different applications, including research, therapeutic and other applications. Accordingly, the present invention represents a significant contribution to the art.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method of identifying an antigen that is present in first and second samples in different amounts, comprising,
   a) immunizing a first and second rabbit with a first and a second sample of human cells or a fraction thereof to generate a first and a second population of rabbit antibodies, respectively;
   b) distinguishably labeling said first and second population of antibodies,
   c) contacting said first and second populations of labeled antibodies with a plurality of non-human mammalian cells producing a library of human proteins on their cell surfaces;
   d) sorting a non-human mammalian cell that is differentially bound by said first and second populations of antibodies, and
   e) identifying a human protein on a surface of said non-human mammalian cell, wherein said human protein is an antigen that is present in said first and second samples in differing amounts.

2. The method of claim 1, wherein said sorting is based on a ratio of levels of binding of said first and second population of antibodies to said non-human mammalian cell, wherein said first and second population of antibody independently provide a signal, and the ratio of the two signals indicates said non-human mammalian cell that is differentially bound.

3. The method of claim 1, wherein said first sample is an abnormal cell and said second sample is a normal cell.

4. A method of identifying a differentially expressed protein, comprising,
   a) distinguishably labeling a first and a second population of polyclonal antibodies that are reactive against a cancerous human cell and a non-cancerous human cell, respectively;
   b) contacting said first and second populations of labeled antibodies with a plurality of non-human mammalian cells producing human proteins; and
   c) identifying a non-human mammalian cell producing a protein that is differentially bound by said first and second populations of antibodies,
   wherein said protein is differentially expressed.

5. The method of claim 4, wherein said human proteins are produced on a surface of said non-human mammalian cells.

6. The method of claim 5, wherein said non-human mammalian cell is a rabbit cell.

7. The method of claim 4, wherein said plurality of non-human mammalian cells express a library of recombinant human proteins.

* * * * *